United States Patent
Wang et al.

(10) Patent No.: US 10,292,804 B2
(45) Date of Patent: May 21, 2019

(54) EMBOLECTOMY DEVICES

(71) Applicants: STRYKER CORPORATION, Kalamazoo, MI (US); STRYKER EUROPEAN HOLDINGS I, LLC, Kalamazoo, MI (US)

(72) Inventors: Jiaxu Wang, Salt Lake City, UT (US); Ryan M. Grandfield, Livermore, CA (US)

(73) Assignees: Stryker Corporation, Kalamazoo, MI (US); Stryker European Holdings I, LLC, Kalamazoo, MI (US)

( * ) Notice: Subject to any disclaimer, the term of this patent is extended or adjusted under 35 U.S.C. 154(b) by 136 days.

(21) Appl. No.: 15/270,322

(22) Filed: Sep. 20, 2016

(65) Prior Publication Data

US 2017/0079766 A1    Mar. 23, 2017

Related U.S. Application Data

(60) Provisional application No. 62/221,529, filed on Sep. 21, 2015.

(51) Int. Cl.
*A61B 17/22* (2006.01)
*A61F 2/01* (2006.01)
*A61B 17/221* (2006.01)

(52) U.S. Cl.
CPC .............. *A61F 2/01* (2013.01); *A61B 17/221* (2013.01); *A61B 2017/2215* (2013.01);
(Continued)

(58) Field of Classification Search
CPC .............. A61B 17/221; A61B 17/3207; A61B 2017/22034; A61B 2017/22035;
(Continued)

(56) References Cited

U.S. PATENT DOCUMENTS 5,800,525 A * 9/1998 Bachinski ................. A61F 2/01
606/200
6,179,859 B1   1/2001 Bates et al.
(Continued)

FOREIGN PATENT DOCUMENTS

EP          2361590 A1    8/2011

OTHER PUBLICATIONS

PCT International Search Report and Written Opinion for International Appln. No. PCT/US2016/052618, Applicant Stryker Corporation, dated Nov. 28, 2016 (8 pages).

*Primary Examiner* — Melanie R Tyson
(74) *Attorney, Agent, or Firm* — Vista IP Law Group LLP

(57) ABSTRACT

An embolectomy device includes a clot engaging structure comprising a plurality of interconnected struts forming an open cell structure having an inner lumen, wherein the clot engaging structure is biased to expand or otherwise expandable from a radially constrained configuration to a radially expanded configuration when released from a delivery catheter into a blood vessel; and a support structure positioned within the inner lumen of the clot engaging structure, the support structure comprising a plurality of connectors connected to respective struts of the clot engaging structure, wherein the support structure connectors are biased to move or otherwise movable from a radially constrained configuration to a radially expanded configuration to thereby cause or otherwise assist and/or facilitate and maintain expansion of the open cell clot engaging structure.

4 Claims, 7 Drawing Sheets

(52) U.S. Cl.
CPC ............... *A61B 2017/22034* (2013.01); *A61F 2002/011* (2013.01); *A61F 2002/016* (2013.01)

(58) Field of Classification Search
CPC . A61B 2017/2215; A61B 2017/320716; A61F 2/01; A61F 2/013; A61F 2002/011; A61F 2002/016; A61F 2002/018
USPC .................................................. 606/127, 200
See application file for complete search history.

(56) References Cited

U.S. PATENT DOCUMENTS

| | | | |
|---|---|---|---|
| 6,544,279 B1 | 4/2003 | Hopkins et al. | |
| 6,605,111 B2 | 8/2003 | Bose et al. | |
| 6,610,077 B1 | 8/2003 | Hancock et al. | |
| 6,652,548 B2 | 11/2003 | Evans et al. | |
| 7,063,707 B2 | 5/2006 | Bose et al. | |
| 7,399,308 B2 | 7/2008 | Borillo et al. | |
| 7,862,578 B2 | 1/2011 | Tsugita | |
| 7,883,526 B2 | 2/2011 | Jones et al. | |
| 7,901,426 B2 | 3/2011 | Gilson et al. | |
| 7,927,349 B2 | 4/2011 | Brady et al. | |
| 8,062,328 B2 | 11/2011 | Hallisey | |
| 8,337,520 B2 | 12/2012 | Cully et al. | |
| 8,430,837 B2 | 4/2013 | Jenson et al. | |
| 8,523,936 B2 | 9/2013 | Schmid et al. | |
| 8,529,596 B2 | 9/2013 | Grandfield | |
| 8,771,289 B2 | 7/2014 | Mohiuddin et al. | |
| 8,777,976 B2 | 7/2014 | Brady et al. | |
| 8,852,205 B2 | 10/2014 | Brady et al. | |
| 2004/0049226 A1 | 3/2004 | Brady et al. | |
| 2005/0267491 A1 | 12/2005 | Kellett et al. | |
| 2007/0219642 A1 | 9/2007 | Richter | |
| 2010/0268265 A1 | 10/2010 | Krolik et al. | |
| 2012/0083868 A1 | 4/2012 | Shirivastava et al. | |
| 2012/0222969 A1 | 9/2012 | Osborne et al. | |
| 2013/0030460 A1* | 1/2013 | Marks | A61B 17/221 606/200 |
| 2013/0060276 A1 | 3/2013 | Hocking | |
| 2014/0005674 A1 | 1/2014 | Angel et al. | |
| 2014/0052103 A1 | 2/2014 | Cully et al. | |
| 2014/0128905 A1 | 5/2014 | Molaei | |

* cited by examiner

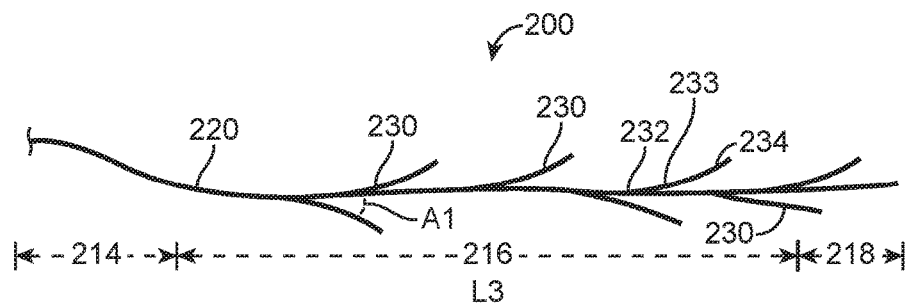
FIG. 4A
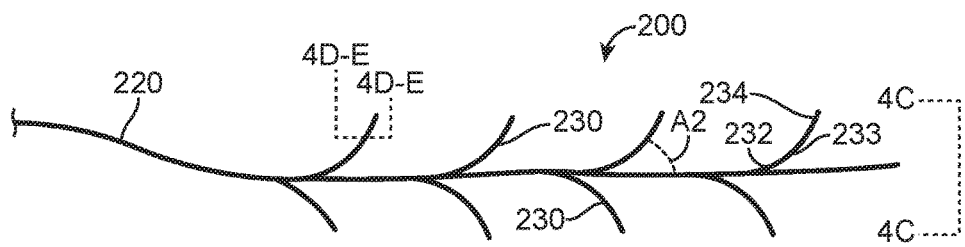
FIG. 4B
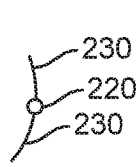 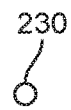 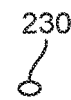
FIG. 4C    FIG. 4D    FIG. 4E
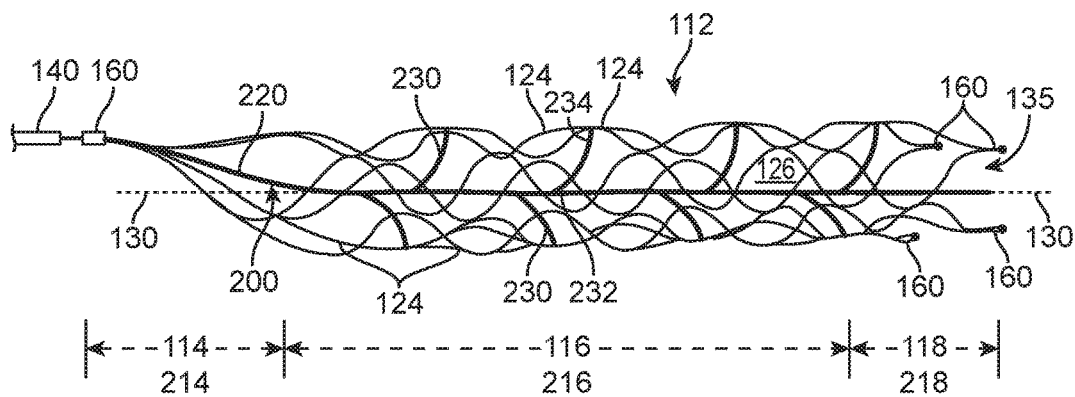
FIG. 5

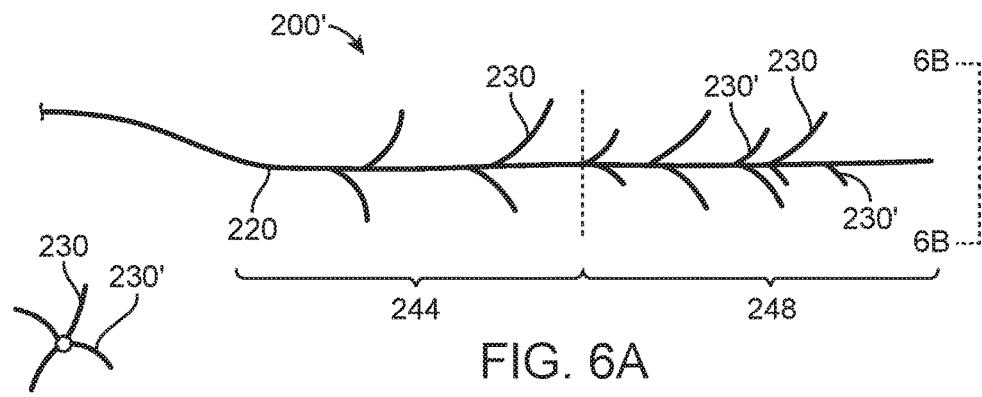
FIG. 6A
FIG. 6B
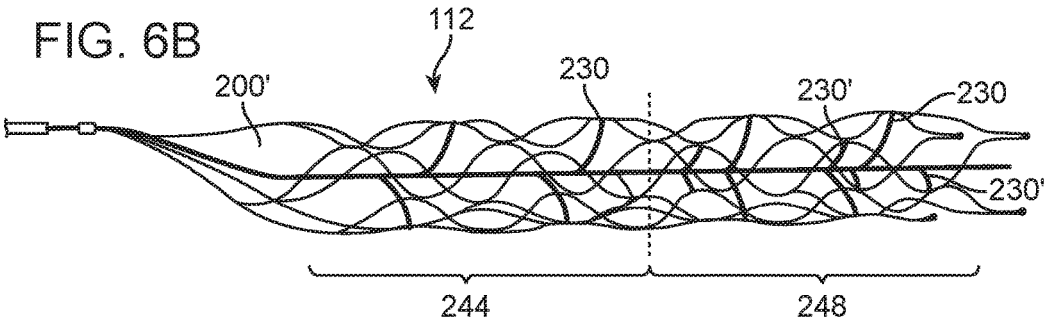
FIG. 7
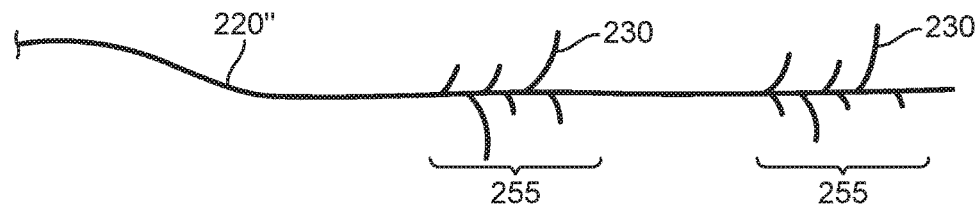
FIG. 8
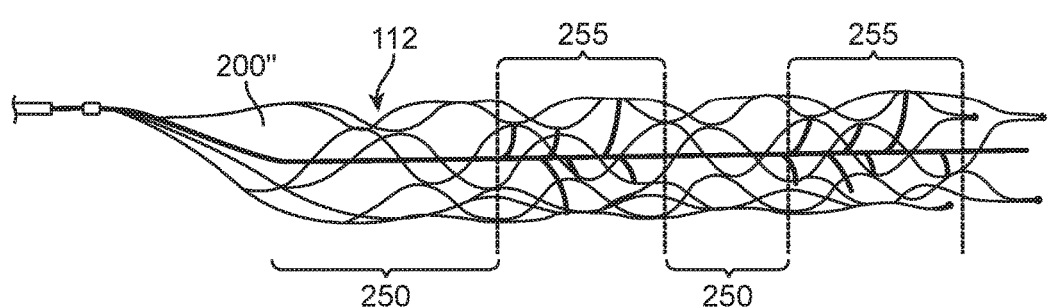
FIG. 9

EMBOLECTOMY DEVICES

RELATED APPLICATION DATA

The present application claims the benefit under 35 U.S.C. § 119 to U.S. provisional patent application Ser. No. 62/221,529 filed Sep. 21, 2015. The foregoing application is hereby incorporated by reference into the present application in its entirety.

FIELD

The inventions disclosed herein relate generally to medical devices configured for removing embolic obstructions from the vasculature.

BACKGROUND

Blood thrombus, embolus or clots may occur in a person's vasculature system. Sometimes such clots are harmlessly dissolved in the blood stream. Other times, however, such clots may lodge in a blood vessel, where they can partially or completely occlude the flow of blood, referred to as an ischemic event. If the partially or completely occluded vessel feeds blood to sensitive tissue such as, the brain, lungs or heart, serious tissue damage may result. Such ischemic events may also be exacerbated by atherosclerosis, a vascular disease that causes the vessels to become narrowed and/or tortuous. The narrowing and/or increased tortuousness of the blood vessels may, in certain circumstances, lead to the formation of atherosclerotic plaque that can cause further complications.

Known embolectomy devices may be used in a variety of applications to remove blood clots or other foreign bodies from blood vessels. Such devices includes ones cylindrical scaffold embolectomy devices, such those illustrated and described in U.S. Pat. No. 8,529,596 to Grandfield, which is fully incorporated herein by reference.

FIGS. 1A-B illustrate an exemplary prior art embolectomy device 12 that is manufactured and sold by the Neurovascular Intervention Division of Stryker Corporation (http://www.stryker.com/en-us/products/Neurovascular-Intervention/index.htm). FIG. 1A shows the embolectomy device 12 in a two-dimensional plane view, and FIG. 1B shows the device 12 a three-dimensional expanded tubular configuration. The embolectomy device 12 is composed of shape memory, self-expandable and biocompatible materials, such as Nitinol. The embolectomy device 12 is preferably manufactured by laser cutting a tube or a sheet of shape memory material. The embolectomy device 12 is coupled to an elongate flexible wire 40 that extends proximally from device 12; the wire 40 is configured to push and pull the embolectomy device 12 through sheaths and/or catheters into a target site in a blood vessel.

As shown in FIG. 1A, the embolectomy device 12 includes a includes a proximal end portion 14, a main body portion 16 and a distal end portion 18, the main body portion including a plurality of longitudinal undulating elements 24 (e.g., wires, struts) with adjacent undulating elements being out-of-phase with one another and connected in a manner to form a plurality of diagonally disposed cell structures 26 extending between the respective proximal and distal end portions of the device. The cell structures 26 in the main body portion 16 and distal end portion 18 of the embolectomy device 12 extend continuously and circumferentially around a longitudinal axis 30 of the device 12 (FIGS. 1A-B).

In particular, the cell structures 26 in the proximal end portion 14 extend less than circumferentially around the longitudinal axis 30 of the device 12. The dimensional and material characteristics of the cell structures 26 of the main body portion 16 are selected to produce sufficient radial force (e.g., radial force per unit length of between 0.005 N/mm to 0.050 N/mm, preferable between 0.030 N/mm to 0.050 N/mm) and contact interaction to cause the cell structures 26, and/or the elements 24, to engage with an embolic obstruction residing in the vasculature in a manner that permits partial or full removal of the embolic obstruction from the patient. As best seen in FIG. 1B, the embolectomy device 12 has an overall length L1 of about 32 millimeters with the main body portion 16 length L2 measuring about 20 millimeters. Usually, the length of the main body portion 16 is generally between about 2.5 to about 3.5 times greater than the length of the proximal end portion 14.

FIG. 2 illustrates the embolectomy device 12 of FIGS. 1A-B disposed in a target site of a tortuous vascular anatomy of a patient capturing an embolic obstruction or clot 75. In an unexpanded or radially compressed configuration (not shown), such as when the embolectomy device 12 is disposed within a delivery catheter 80, the embolectomy device 12 has an unexpanded outer diameter (UOD) between 0.4 to 0.7 millimeters. In a radially expanded configuration (FIGS. 1B-2), the embolectomy device 12 has an expanded outer diameter (EOD) between 2.5 to 5.0 millimeters. The embolectomy device 12 produces sufficient radial force and contact interaction to cause the strut elements 24 and/or cell structures 26 to engage/snare/encapsulate/capture/pinch and/or entrap the embolic obstruction 75 disposed within the blood vessel 70, allowing removal of the embolic obstruction 75 from the patient. The diameter of the main body portion 16 in a fully expanded configuration is about 4.0 millimeters with the cell pattern, elements 24 dimensions and material being selected to produce a radial force of between 0.040 N/mm to 0.050 N/mm when the diameter of the main body portion is reduced to between 1.0 millimeters to 1.5 millimeters. The cell pattern 26, strut dimensions 24 and material(s) are selected to produce a radial force of between 0.010 N/mm to 0.020 N/mm when the diameter of the main body portion 16 is reduced to 3.0 millimeters. Having a strut thickness to width ratio of greater than one promotes integration of the strut elements 24 into the embolic obstruction 75.

Regardless of the technique used to manufacture the embolectomy device 12, the manner in which the strut elements 24 interconnect determines the device's longitudinal and radial rigidity and flexibility. Radial rigidity is needed to provide the radial force needed to engage the clot or embolic obstruction 75, but radial flexibility is needed to facilitate radial compression of the device 12 for delivery into a target site. Longitudinal rigidity is needed to pull an engaged clot or embolic obstruction 75 from the blood vessel 70, but longitudinal flexibility is needed to facilitate delivery of the device 12 (e.g., through tortuous vasculature). Embolectomy device 12 patterns are typically designed to maintain an optimal balance between longitudinal and radial rigidity and flexibility for the device 12. However, in certain applications, after deployment of the device 12 into the blood vessel 70, and once the embolectomy device 12 is subjected to tension/force for retraction or withdrawal, the device 12, particularly, the main body portion 16, tends to stretch creating a smaller profile or outer diameter (OD), similar to the unexpanded outer diameter (UOD) described above (e.g., between 0.4 to 0.7 millimeters).

FIG. 3A illustrates the embolectomy device 12 of FIGS. 1A-B and 2, disposed in a blood vessel 70 distally located from the catheter 80 and having a smaller profile/OD. The stretching of the device 12 and smaller profile/OD may cause the device 12 to be withdrawn past the embolic obstruction 75 without engaging or capturing the obstruction 75, as shown in FIGS. 3A and 3D. FIG. 3B-D are cross-sectional views of the blood vessel 70 having a lumen 72 with the embolic obstruction 75 therein. In an embolectomy procedure for removing the embolic obstruction 75 from the blood vessel lumen 72, the delivery catheter 80 is advanced through the lumen 72, until the distal portion of the catheter 80 is disposed in a target site adjacent to the obstruction 75, with the radially compressed embolectomy device 12 disposed within the catheter 80, as shown in FIG. 3C. The embolectomy device 12 is then pushed distally relative to the catheter 80, or the catheter 80 is withdrawn proximally relative to the embolectomy device 12 (or some of each), in order to deploy the device 12 out of the catheter 80 and into the blood vessel lumen 72, allowing the no-longer radially constrained embolectomy device 12 to radially expand within the blood vessel lumen 72 in order to engage, ensnare and capture the obstruction 75.

However, in certain applications (e.g., hard/dense embolic obstruction 75) the radial expansion force 33 of embolectomy device 12 is not sufficient to overcome the hardness and resistive force 36 of the embolic obstruction 75 to allow the struts of device 12 to penetrate into and integrate with the clot 75, causing the device 12 to instead take the path of least resistance by extending around the obstruction 75, as shown in FIG. 3D. The undesirable elongated profile/OD of the device 12 when extending around the obstruction 75 tends to pass the embolic obstruction 75 without engaging, ensnaring or capturing the obstruction 75 when the device 12 is withdrawn.

Accordingly, there is a need to prevent undesirable stretching, elongation and/or reduction of the profile/OD of embolectomy devices when subjected to tension after deployment within a blood vessel, while also allowing for a desired reduction of the profile/OD when the device is re-sheathed for repositioning and/or withdrawal.

SUMMARY

In an exemplary embodiment of the disclosed inventions, an embolectomy device includes a clot engaging structure comprising a plurality of interconnected struts forming an open cell structure having an inner lumen, wherein the clot engaging structure is biased to expand, or is otherwise expandable from, a radially constrained configuration to a radially expanded configuration when released from a delivery catheter into a blood vessel; and a support structure positioned within the inner lumen of the clot engaging structure, the support structure comprising a plurality of connectors connected to respective struts of the clot engaging structure, wherein the support structure connectors are biased to move or otherwise movable from a radially constrained configuration to a radially expanded configuration to thereby cause or otherwise assist and/or facilitate expansion of the clot engaging structure when the clot engaging structure is released from a delivery catheter into a blood vessel.

In some embodiments, the support structure further comprises an elongate central support member that extends at least partially through, and is movable relative to, the lumen of the clot engaging structure, wherein each connector of the plurality of connectors has a first end connected to the central support member and a second end connected to a respective strut of the clot engaging structure. In such embodiments, the first ends of the plurality of connectors may be connected to the central support member at respective axially and/or circumferentially offset locations along the central support member. In order to prevent the support structure from interfering with retrieval of the clot engaging structure into the catheter after the clot is engaged, the connectors preferably form obtuse angles with a segment of the central support member extending proximally from the connector, i.e., wherein the obtuse angles formed between the respective connectors and the central support member is greater when the support structure is in the radially constrained configuration than when the support structure is in the radially expanded configuration.

In alternative embodiments, no central support member is provided, and instead, each connector of the plurality of connectors has a first end connected to a respective first strut of the clot engaging structure and a second end connected to a respective second strut of the clot engaging structure. In such embodiments, one or more of the connectors may form an angle at their respective midpoint. In particular, respective middle portions of one or more of the connectors may include a flexible section, bending point, living hinge or other suitable joint allowing hinge-like movement of the respective connector relative to the clot engaging structure.

It should be appreciated that incorporating the disclosed embodiments of the support structure into the clot retriever not only causes or assists and/or facilitates radial expansion of the struts of clot retrieving structure, but in particular facilitates opening of the cells formed between the struts—and maintaining the cells open to better engage/ensnare the blood clot material, especially if the clot is hardened which may otherwise cause the cells to collapse.

Other and further aspects and features of embodiments of the disclosed inventions will become apparent from the ensuing detailed description in view of the accompanying figures.

BRIEF DESCRIPTION OF THE DRAWINGS

FIG. 3A-3D are cross-sectional views of the prior art embolectomy device of

FIGS. 1A-1B positioned within a blood vessel adjacent an embolic obstruction.

FIGS. 4A-4E are respective perspective, planar and cross-sectional views of a support structure for embolectomy devices, constructed according to one embodiment of the disclosed inventions.

FIG. 5 is a perspective view of an embolectomy device having the support structure of FIGS. 4A-4E, constructed according to one embodiment of the disclosed inventions.

FIGS. 6A-6B show perspective cross-sectional views of a support structure, constructed according to another embodiment of the disclosed inventions.

FIG. 7 is a perspective view of an embolectomy device having the support structure of FIG. 6, constructed according to yet another embodiment of the disclosed inventions.

FIG. 8 is a perspective view of a support structure, constructed according to yet another embodiment of the disclosed inventions.

FIG. 9 is a perspective view of another embodiment of an embolectomy device having the support structure of FIG. 8, constructed according to still another embodiment of the disclosed inventions.

DETAILED DESCRIPTION OF THE ILLUSTRATED EMBODIMENTS

Figure 1A:
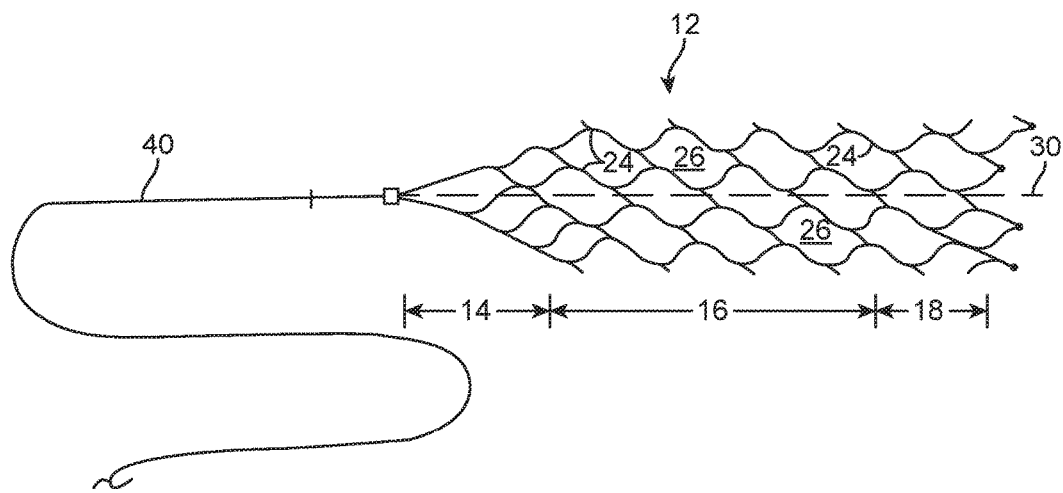
FIGS. 1A-1B show perspective views of a prior art embolectomy device.
Figure 1B:
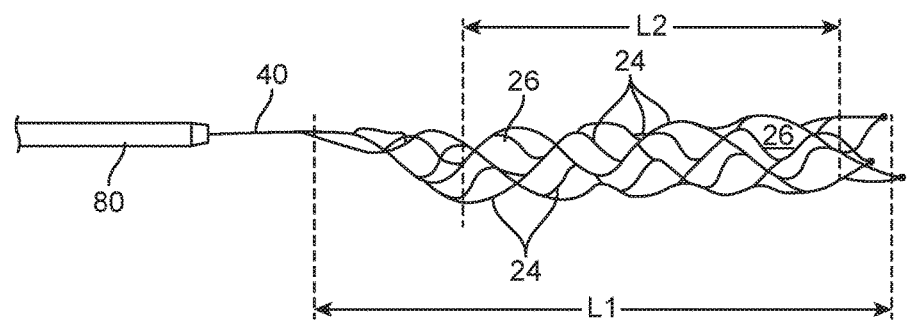
Figure 2:
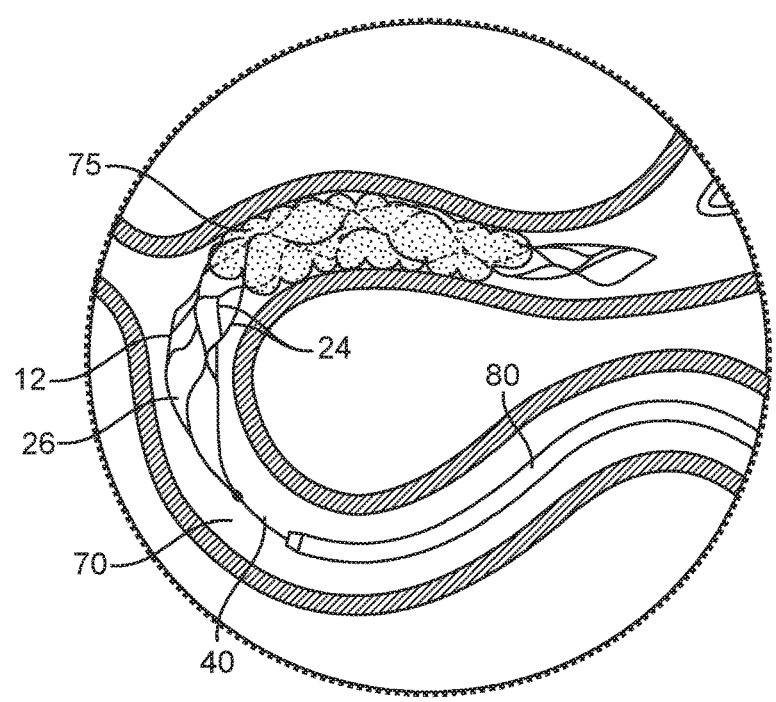
FIG. 2 is a cross-sectional view of the prior art embolectomy device depicted in FIGS. 1A-1B, while capturing an embolic obstruction within a blood vessel.
Figure 3A:
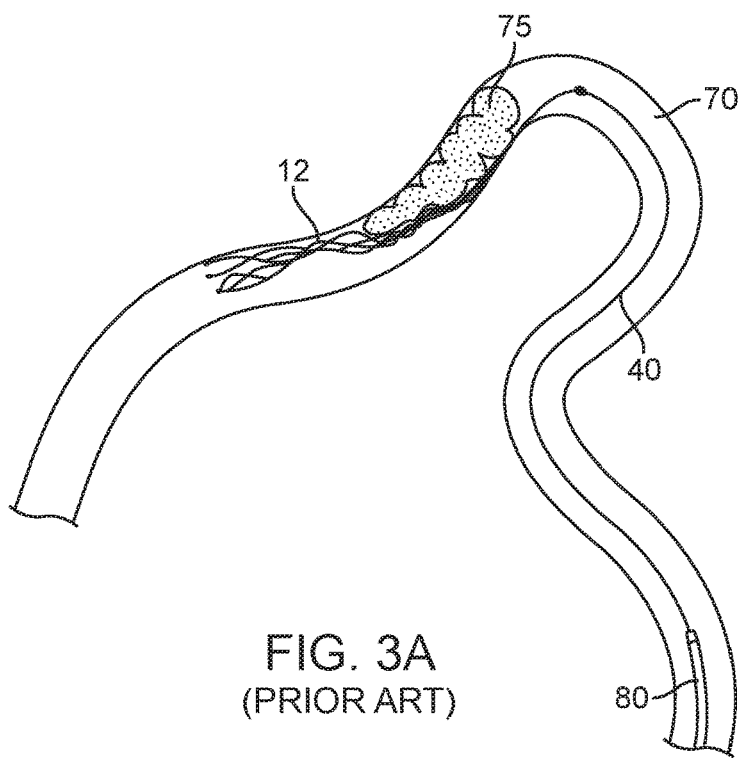
Figure 3D:
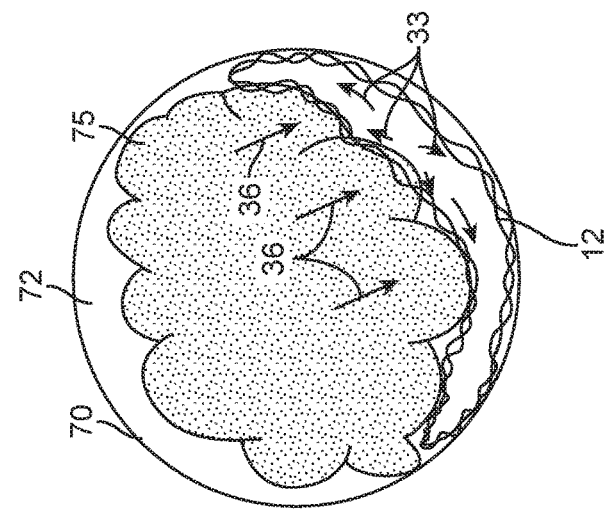
Figure 3C:
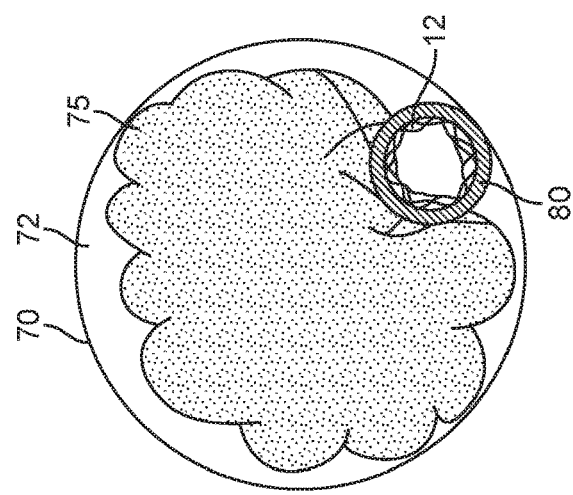
Figure 3B:
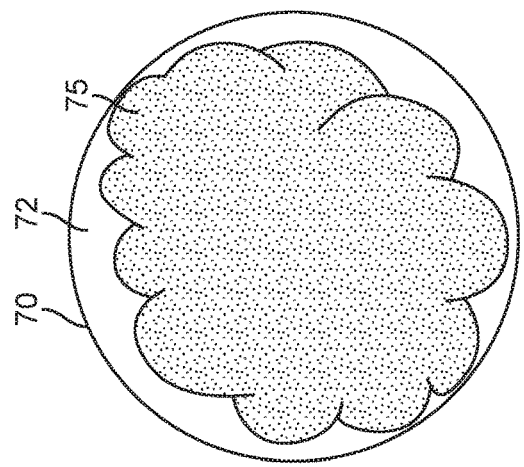

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure. The recitation of numerical ranges by endpoints includes all numbers within that range (e.g., 1 to 5 includes 1, 1.5, 2, 2.75, 3, 3.80, 4, and 5). As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

FIG. 4A-E illustrate a support structure 200 for embolectomy devices, constructed in accordance with one embodiment of the disclosed inventions. The support structure 200 includes an elongated central member 220 having a plurality of elements 230 extending therefrom. The central member 220 includes a proximal end portion 214, a main body portion 216, and a distal end portion 218. The extending elements 230 have respective first ends 232 coupled to the central member 220 (FIGS. 4A-4C and 5), respective second ends 234 coupled to the strut elements 124 of the embolectomy device 112 (FIG. 5), and respective middle portions 233 extending between the first and second ends (FIGS. 4A-4C and 5). The first ends 232 of the extending elements 230 may include a flexible section, bending point, living hinge or other suitable joint allowing hinge-like movement of the extending elements 230 relative to the central member 220.

The extending elements 230 of FIG. 4A-4C are alternatively disposed along a length L3 of the elongated central member 220, having the respective first ends 232 proximately disposed from the respective second ends 234, such as the veins of a leaf. The extending elements 230 may further include a concave curvature (e.g. positive unipolar concave, soft curvature) extending from the respective first ends 232 to the respective second ends 234, as shown in FIGS. 4A-4C. The extending elements 230 may include a circular (FIG. 4D), oval (FIG. 4E) or other suitable cross-sectional configuration. It should be appreciated that the cross-sectional configuration of the extending elements 230 may be a continuous configuration from the first ends 232 to the second end 234, or may vary along its length. For example, the cross sectional configuration of the extending element 230 can be circular at the first 232 and second 234 ends and can be oval at the middle portion 233.

The support structure 200 may be formed of a unitary component (e.g., laser cut of cylindrical structure or sheet, 3D printing, extrusion or the like), or may also include separate components that are welded, bonded or otherwise engaged to one another. For example, the extending elements 230 may be bonded to the central member 220 in a hinged-like fashion. The support structure 200 has a delivery configuration in which the plurality of extending elements 230 are radially constrained (FIG. 4A), and a deployed configuration in which the plurality of elements 230 are radially expanded (FIG. 4B). The extending elements 230 are disposed in an angle "A" relative to the central member 220. For example, the angle of the extending elements 230 may range between 10° (A1—FIG. 4A) to 75° (A2—FIG. 4A); other suitable angles are contemplated. The extending elements 230 may be biased to expand outwardly, as shown in FIG. 4B.

The support structure 200 may be composed from any number of biocompatible, compressible, elastic materials or combinations thereof, including polymeric materials, metals, and metal alloys, such as stainless steel, tantalum, or a nickel titanium alloy such as a super-elastic nickel titanium alloy known as Nitinol. The support structure 200 may include radio-opaque markers or be coated with a layer of radiopaque materials. It should be appreciated that the support structure 200, including the central member 220 and the extending elements 230 may have an alternative shapes, and other suitable configurations. Other variations of the support structure 200, such as the configuration of the extending elements 230 (e.g., locations, shapes, materials) are contemplated, such as the exemplary configurations depicted in FIGS. 6 and 8. As used in this specification, the term "support structure" may refer to any device or component to which one or more components may be directly or indirectly coupled, attached or secured. Further, as used in this specification, the term "coupled" may refer to one or more components that may be directly or indirectly attached, secured, or otherwise, connected.

FIG. 5 illustrates an embolectomy device having the support structure of FIGS. 4A-4C, according to the disclosed inventions. The embolectomy device 112 includes a cylindrical scaffold formed from by a plurality of elongated strut elements 124. The strut elements 124 may be a plurality of longitudinal undulating elements with a set of adjacent undulating elements being out-of-phase with one another and interconnected in a manner to form a plurality of diagonally disposed cell structures 126. The embolectomy device 112 includes a proximal end portion 114, a main body portion 116, a distal end portion 118, and having a lumen 135 extending from the proximal end portion 114 to the distal end portion 118. The embolectomy device 112 is coupled to an elongate flexible wire 140 that extends proximally from device 112; the wire 140 is configured to push and pull the embolectomy device 112 through sheaths and/or catheters into a target site in a blood vessel. The embolectomy device 112 includes one or more radio-opaque markers 160.

The cell structures 126 extend continuously and circumferentially around a longitudinal axis 130 of the device 112. The dimensional and material characteristics of the strut elements 124 and/or the cell structures 126 of the main body portion 116 are selected to produce sufficient radial force (e.g., radial force per unit length of between 0.005 N/mm to 0.050 N/mm, preferable between 0.030 N/mm to 0.050 N/mm) and contact interaction to cause the cell structures 126, and/or the elements 124, to engage with an embolic obstruction residing in the vasculature permitting partial or full removal of the embolic obstruction from the patient.

The embolectomy device 112 can be woven from wires, cut out of tubes, or cut out of sheets using a variety of techniques, including laser cutting or etching a pattern onto a tube or sheet to form struts from the remaining material, or other suitable techniques. The embolectomy device 112 may be composed from any number of biocompatible, compressible, elastic materials or combinations thereof, including polymeric materials, metals, and metal alloys, such as stainless steel, tantalum, or a nickel titanium alloy such as a super-elastic nickel titanium alloy known as Nitinol.

As shown in FIG. 5, the embolectomy device 112 includes the support structure 200 of FIGS. 4A-4C. The support structure 200 is disposed within the lumen 135 of the embolectomy device 112. In one embodiment, the central member 220 of the support structure 200 is disposed along the longitudinal axis 130 of the embolectomy device 112. The support structure 200, particularly, the proximal end portion 214 of the central member 220, is coupled to the wire 140, while the second ends 234 of the respective extending elements 230 are coupled to a respective strut element 124. The support structure 200 provides a suitable support for the embolectomy device 112 preventing stretching of the device 112 while subjected to pull, withdrawal or retraction forces that creates an undesirable smaller profile/OD of the device (FIG. 3). When pull, axial withdrawal or retraction forces are applied to the embolectomy device 112 via the wire 140, such forces are distributed between the support structure 200 and the strut elements 124 of the embolectomy device 112.

In one embodiment, a greater percentage of the pull, withdrawal or retraction forces is transmitted to the support structure 200 as opposed to the strut elements 124, assisting the embolectomy device 112 to retain the deployed configuration, and preventing stretching of the device 112 and undesirable smaller profile/OD (e.g., passing past the embolic obstruction without engaging, ensnaring or capturing the obstruction). Additionally, the embolectomy device 112 comprising the support structure 200 having extending elements 230 with concave curvature that extend distally (FIGS. 4A-4B and 5) allows for desirable reduction of the profile/OD, such as, when the device 112 is re-sheathed for repositioning and/or withdrawal.

FIGS. 6A and 7 illustrate a support structure for embolectomy devices, constructed in accordance with another embodiment of the disclosed inventions. For ease in illustration, the features, functions, and configurations of the support structure 200' are the same as in the support structure 200 of FIGS. 4A-4E are given the same reference numerals. The support structure 200' includes an elongated central member 220 having a plurality of elements 230 extending therefrom. The extending members 230 are alternatively disposed along the central member 220. In one embodiment, the elongated members 230 are alternatively and radially disposed along the central member 220, making some of the elongated members 230' look shorter in the perspective view of FIGS. 6A and 7. The elongated members 230' are approximately the same length as the elongated members 230, as better shown in the cross-sectional view of the support structure 200' shown in FIG. 6B. In another embodiment, the elongated central member 220 includes a plurality of longer extending elements 230 and shorter extending elements 230'' alternatively disposed along the central member 220 (not shown).

The support structure 200' comprises a proximal portion 244, and a distal portion 248. The extending elements 230/230' are alternatively and progressively disposed along the central member 220 having less extending elements 230 at the proximal portion 244 and more extending elements at the distal portion 248, so that the embolectomy device 112 have greater support at the distal portion preventing stretching of the device 112 and undesirable smaller profile/OD (e.g., passing past the embolic obstruction without engaging, ensnaring or capturing the obstruction).

FIGS. 8 and 9 illustrate a support structure for embolectomy devices, constructed in accordance with yet another embodiment of the disclosed inventions. For ease in illustration, the features, functions, and configurations of the support structure 200'' are the same as in the support structure 200 of FIGS. 4A-4E, and/or 200' of FIGS. 6A-6B and 7 are given the same reference numerals. The support structure 200'' includes an elongated central member 220 having a plurality of elements 230 extending therefrom. The extending members 230 are alternatively disposed along the central member 220.

In one embodiment, the elongated members 230 are alternatively and radially disposed along the central member 220, making some of the elongated members 230' look shorter, similarly than in the perspective view of FIGS. 6A and 7. In another embodiment, the elongated central member 220 includes a plurality of longer extending elements 230 and shorter extending elements 230'' alternatively disposed along the central member 220 (not shown). The support structure 200'' comprises alternating supported segments 255 having extending elements 230/230' and unsupported segments 250 without extending elements, as shown in FIGS. 8 and 9. Having the plurality of supported 255 and unsupported 250 segments provides for the embolectomy device 112 of FIG. 9 to have a variable radial force, which may assist and facilitate embolic clot integration to the device 112.

Figure 10:
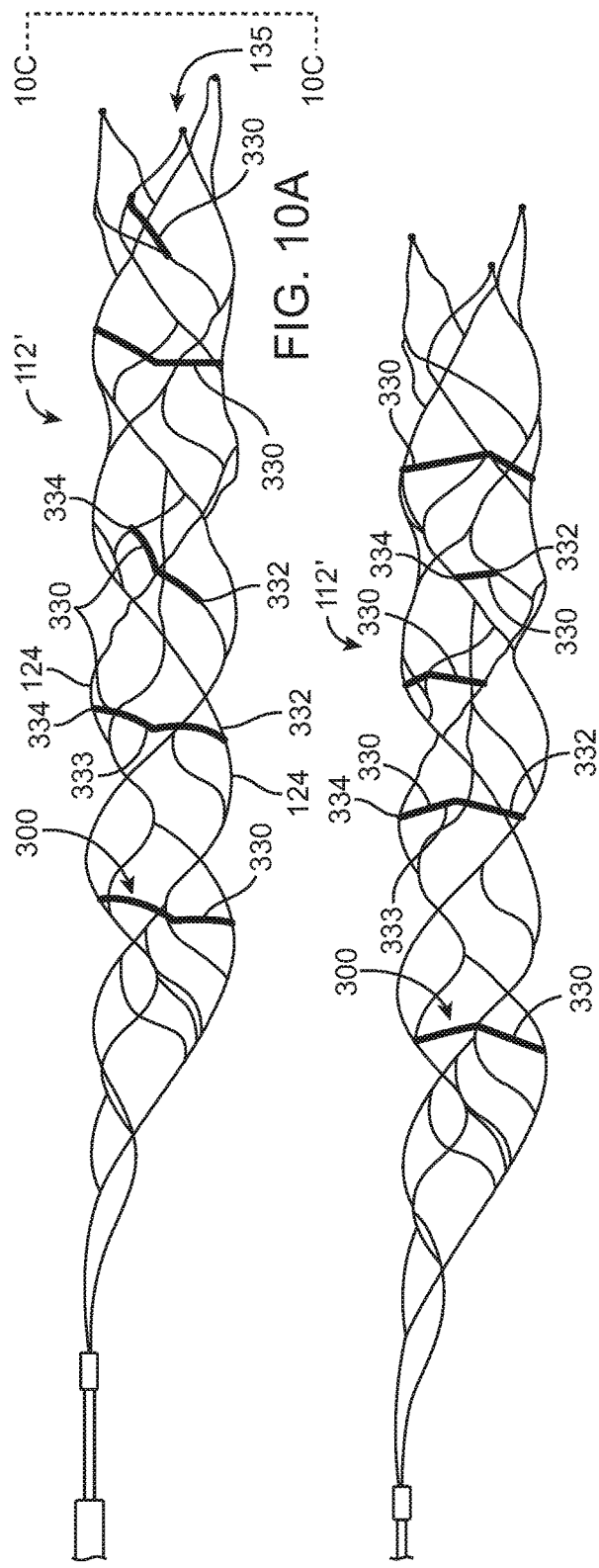
FIGS. 10A-10D are perspective cross-sectional views of yet another embodiment of an embolectomy device, including an alternative support structure constructed according to further embodiments of the disclosed inventions.

FIGS. 10A-10D illustrates an embolectomy device 112' having an alternative support structure 300 constructed in accordance with another embodiment of the disclosed inventions. For ease in illustration, the features, functions, and configurations of the embolectomy device 112' that are the same as in the embolectomy device 112 of FIGS. 5, 7 and 9 are given the same reference numerals. The support structure 300 is disposed within the lumen 135 of the embolectomy device 112', and includes a plurality of extending elements 330 transversely disposed in the lumen 135 when the embolectomy device 112' is in the deployed configuration, as best seen in FIG. 10C. The extending elements 330 have respective first ends 332 coupled to a respective strut element 124, respective second ends 334 coupled to the strut elements 124 of the embolectomy device 112', and respective middle portions 333 extending between the first and second ends (FIGS. 10A-10C).

In one embodiment, the first ends 332 of the extending elements 330 are disposed about 180° in relation to their respective second ends 334 when the device 112' is in the deployed configuration. It should be understood that the extending elements 330 may form other angles between their respective first 332 and second 334 ends when the device 112' is deployed, for example, between 170° to 190°, or any suitable angle configured to assist with the radial expansion and/or support of the device 112'. The middle portions 333 of the extending elements 330 may include a flexible section, bending point, living hinge or other suitable joint allowing hinge-like movement of the extending elements 330 relative to the embolectomy device 112'. The middle portions 333 of the extending elements 330 may bend towards the proximal end portion 114 of embolectomy device 112', as shown in FIG. 10A. Alternatively, the middle portions 333 of the extending elements 330 may bend towards the distal end portion 118 of embolectomy device 112', as shown in FIG. 10B.

The support structure 300 has a delivery configuration in which the plurality of extending elements 330 are radially constrained (FIG. 10D), and a deployed configuration in which the plurality of elements 330 are radially expanded (FIG. 10A-10C). As depicted in FIG. 10A and 10B, the extending elements 330 are alternatively disposed along the main body portion 116 or length L3 of embolectomy device 112'. The extending elements 330 may further include a concave curvature (e.g. positive unipolar concave, soft curvature) extending from the respective first ends 332 to the respective second ends 334. The extending elements 330 may include a circular, oval or other suitable cross-sectional configuration, as shown in FIGS. 4D-4E for the extending elements 230. It should be appreciated that the cross-sectional configuration of the extending elements 330 may be a continuous configuration from the first ends 332 to the second end 334, or may vary along its length. For example, the cross sectional configuration of the extending element 330 can be circular at the first 332 and second 334 ends, and can be oval or tapered at the middle portion 333.

The extending element 330 of the support structure 300 may be formed of a unitary component when the embolectomy device 112' is manufactured (e.g., laser cut of cylindrical structure or sheet, 3D printing, extrusion or the like), or may also include separate components that are welded, bonded or otherwise engaged to one another. The support structure 300 may be composed from any number of biocompatible, compressible, elastic materials or combinations thereof, including polymeric materials, metals, and metal alloys, such as stainless steel, tantalum, or a nickel titanium alloy such as a super-elastic nickel titanium alloy known as Nitinol. The support structure 300 may include radio-opaque markers or be coated with a layer of radiopaque materials. It should be appreciated that the support structure 300 may have alternative shapes, locations, materials and other suitable configurations. For example, the support structure 300 may include more extending elements 330 at the distal portion than at the proximal portion of the embolectomy device 112', as shown in FIGS. 6 and 7 for the support structure 200'. In another example, the support structure 300 may be include alternating supported segments having extending elements 330 and unsupported segments without extending elements, as shown in FIGS. 8 and 9 for the support structure 200".

The support structure 300 is configured to assist and/or support the radial expansion of the embolectomy device 112' when deployed. The support structure 300 may further prevent the stretching of the embolectomy device 112' while the device 112' subjected to pull, withdrawal or retraction forces that creates an undesirable smaller profile/OD of the device (FIG. 3) by supporting and/or assisting with the radial expansion of the deployed device 112'.

Figure 11:
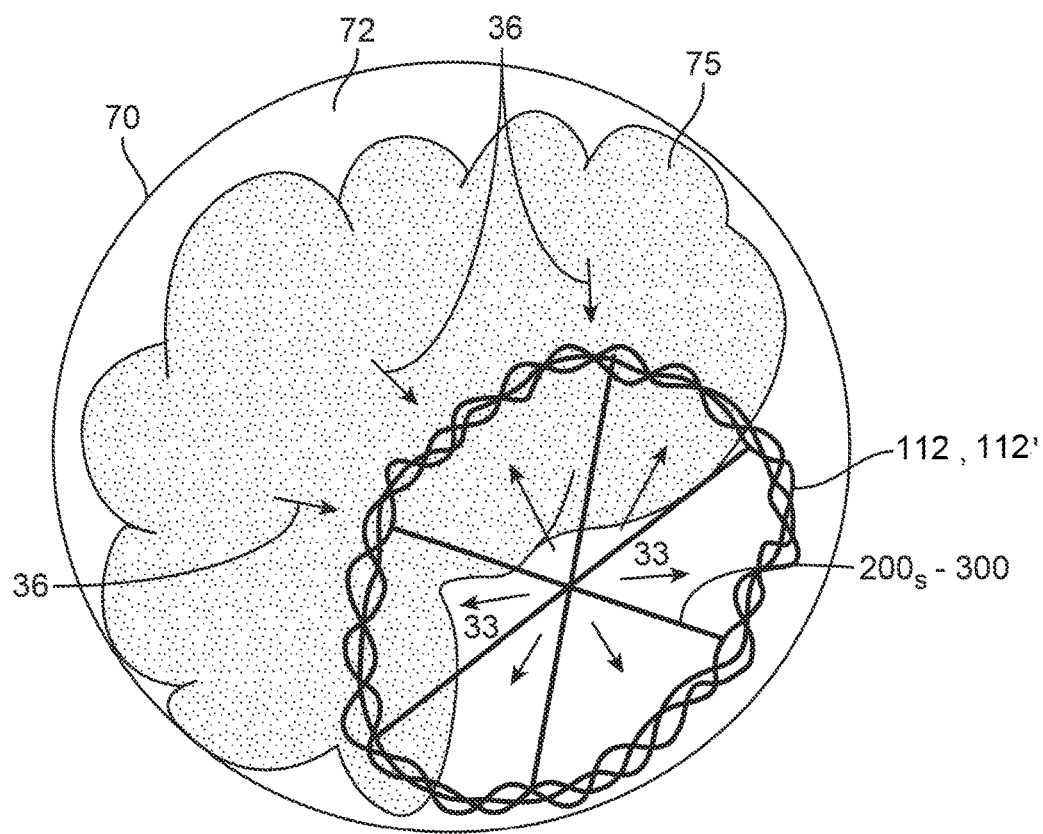
FIG. 11 is a cross-sectional view of the embolectomy device of FIGS. 10A-10D, depicted capturing an embolic obstruction within a blood vessel.

FIG. 11 illustrates an exemplary use of an embolectomy device having a support structure according to the disclosed inventions. As shown in FIG. 11, the embolectomy device may be either of the devices 112/112', having either of the support structures 200/200'/200"/300 (e.g., 200s-300), as described in detailed above. For ease in illustration, the features, functions, and configurations of the embolectomy devices 112/112' and support structures 200s-300 are the same as in the ones described in the embodiments depicted in FIGS. 4A-10C, and are given the same reference numerals.

The embolectomy device 112/112' is either pushed distally relative to the catheter 80, or the catheter 80 is withdrawn proximally relative to the embolectomy device 112/112' (or some of each) (not shown), in order to deploy the device 112/112' out of the catheter 80 and into the lumen 72 of the blood vessel 70, and allow the no-longer radially constrained embolectomy device 112/112' to radially expand within the blood vessel 70 in order to engage, ensnare and capture the obstruction 75. The support structure 200s-300 assists and/or supports the radial expansion forces 33 of the embolectomy device 112/112', and may further assist the device 112/112' to overcome the resistive forces 36 of the embolic obstruction 75, which in turn allows the device to penetrate the obstruction 75, as shown in FIG. 11. The support structures 200s-300 in the embolectomy device 112/112' prevent undesirable stretching, elongation and/or reduction of the profile/OD (FIGS. 3A, 3D) of embolectomy devices, when subjected to tension after deployment within the blood vessel 70, allowing the device 112/112' to radially expand when deployed in order to engage, ensnare and/or capture the obstruction 75. As described above, the support structures 200s-300 are configured to further allow a desirable reduction of the profile/OD when the device 112/112' is re-sheathed for repositioning and/or withdrawal.

It will be appreciated that the support structures depicted in FIGS. 4A-11 may be used in other suitable medical devices, for example, disposed within tubular prosthesis, implants, stents, fluid diverters or the like for both vascular and non-vascular applications.

While embodiments have been shown and described, various modifications may be made without departing from the scope of the inventive concepts disclosed herein. The invention(s), therefore, should not be limited, except as defined in the following claims.

What is claimed is:

1. An embolectomy device, comprising:
   a clot engaging structure comprising a plurality of interconnected struts forming an open cell structure extending around a longitudinal axis of the device and having an inner lumen, wherein the clot engaging structure is biased to expand, or is otherwise expandable from, a radially constrained configuration to a radially expanded configuration when released from a delivery catheter into a blood vessel; and
   a support structure positioned within the inner lumen of the clot engaging structure, the support structure comprising a plurality of connectors connected to respective struts of the clot engaging structure, the plurality of connectors spaced apart longitudinally along the longitudinal axis of the device, wherein the connectors are biased to self-expand from a radially constrained configuration to a radially expanded configuration to thereby cause or otherwise assist and/or facilitate expansion of the clot engaging structure and/or establishing and maintaining an open cell structure thereof when the clot engaging structure is released from a delivery catheter into a blood vessel, and wherein each connector of the plurality of connectors has a first end connected to a respective first strut of the clot engaging structure and a second end connected to a respective second strut of the clot engaging structure without being connected to a central support member.

2. The embolectomy device of claim 1, wherein the respective first and second struts are located on opposing sides of the clot engaging structure.

3. The embolectomy device of claim 1, wherein one or more of the connectors form an angle at their respective midpoint.

4. The embolectomy device of claim 1, wherein each of the connectors comprise a middle portion, and wherein the respective middle portions of one or more of the connectors includes a flexible section, bending point, living hinge or other suitable joint allowing hinge-like movement of the respective connector relative to the clot engaging structure.

* * * * *